(12) United States Patent
Memoli et al.

(10) Patent No.: US 6,268,364 B1
(45) Date of Patent: Jul. 31, 2001

(54) SUBSTITUED TETRAHYDRO-1,3,5-TRIAZIN-2[1H]-THIONES AS ANTI-ATHEROSCLEROTIC AGENTS

(75) Inventors: Kevin A. Memoli, Cranbury, NJ (US); Donald P. Strike, St. Davids, PA (US); Amedeo A. Failli, Princeton Junction, NJ (US); Robert J. Steffan, Langhorne, PA (US)

(73) Assignee: American Home Products Corporation, Madison, WI (US)

( * ) Notice: Subject to any disclaimer, the term of this patent is extended or adjusted under 35 U.S.C. 154(b) by 0 days.

(21) Appl. No.: 09/483,711

(22) Filed: Jan. 14, 2000

Related U.S. Application Data

(62) Division of application No. 08/960,832, filed on Oct. 30, 1997.
(60) Provisional application No. 60/030,902, filed on Nov. 14, 1996.

(51) Int. Cl.[7] ............... A61K 31/53; A61P 3/06; A61P 9/10; C07D 239/40
(52) U.S. Cl. ............... 514/241; 544/220
(58) Field of Search ............... 544/220; 514/241

(56) References Cited

U.S. PATENT DOCUMENTS

| | | | |
|---|---|---|---|
| 3,505,057 | 4/1970 | Luckenbaugh | 544/220 |
| 3,505,323 | 4/1970 | Luckenbaugh | 544/220 |
| 4,193,994 * | 3/1980 | Leeming et al. | 544/220 |

OTHER PUBLICATIONS

Kovalenko, A.L. et al., Aminomethylation of Thiourea Derivatives with N–Methylene–tert–Butylamine, Zhurnal Obshcei Khimii, vol. 61, No. 8 (1991), pp. 1870–1873.

Zakharov, O.S. et al., Khim. Geterotsikl. Soedin., No. 7 (1986) pp. 976–980.

Kuchevskii, B.V. et al., Vulcanization Activity of Some Heterocyclic Compounds Containing a Thioureide Fragment, Kauch, Rezina. 32(10), (1973) 19–21.

* cited by examiner

Primary Examiner—Richard L. Raymond
Assistant Examiner—Venkataraman Balasubramanian
(74) Attorney, Agent, or Firm—Arnold S. Milowsky

(57) ABSTRACT

This invention provides compounds of formula 1 having the structure

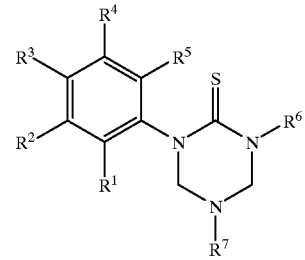

wherein $R^1$, $R^2$, $R^3$, $R^4$, and $R^5$ are each independently, hydrogen, halogen, alkyl, cycloalkyl, alkenyl, alkynyl, phenylalkyl, alkoxy, aryloxy, fluoroalkoxy, trifluoromethyl, alkylthio, alkylsulfony, —$SCF_3$, nitro, alkylamino, or dialkylamino;

$R^6$ is hydrogen, alkyl, cycloalkyl, or arylalkyl; and $R^7$ is alkyl, cycloalkyl, or arylalkyl or a pharmaceutically acceptable salt thereof which are useful as antiatherosclerotic agents.

8 Claims, No Drawings

SUBSTITUED TETRAHYDRO-1,3,5-TRIAZIN-2[1H]-THIONES AS ANTI-ATHEROSCLEROTIC AGENTS

This is a divisional application of prior application Ser. No. 08/960,832, filed Oct. 30, 1997 now pending, which application claims the benefit of U.S. Provisional Application Ser. No. 60/030,902, filed Nov. 14, 1996.

FIELD OF THE INVENTION

This invention is in the field of anti-atherosclerotic agents and specifically relates to compounds, compositions and methods for treating atherosclerotic conditions such as dyslipoproteinimias and coronary heart disease. This invention specifically relates to substituted tetrahydro-1,3,5-triazin-2[1H]-thione derivatives that elevate HDL cholesterol concentration and which may be useful for the treatment of atherosclerotic conditions and coronary heart disease.

BACKGROUND OF THE INVENTION

Numerous studies have demonstrated that both the risk of coronary heart disease (CHD) in humans and the severity of experimental atherosclerosis in animals are inversely correlated with serum HDL cholesterol (HDL-C) concentrations (Russ et al, *Am. J. Med.*, 11 (1951) 480–483; Gofman et al. *Circulation.* 34 (1966), 679–697; Miller and Miller, *Lancet* 1 (1975), 16–19; Gordon et al., *Circulation,* 79 (1989), 8–15; Stampfer et al., *N. Engl. J. Med.,* 325 (1991), 373–381; Badimon et al., *Lab. Invest.,* 60 (1989), 455–461). Atherosclerosis is the process of accumulation of cholesterol within the arterial wall which results in the occlusion, or stenosis, of coronary and cerebral arterial vessels and subsequent myocardial infarction and stroke. Angiographic studies have shown that elevated levels of some HDL particles in humans appear to be correlated to a decreased number of sites of stenosis in the coronary arteries of humans (Miller et al., *Br. Med. J.,* 282 (1981), 1741–1744).

There are several mechanisms by which HDL may protect against the progression of atherosclerosis. Studies in vitro have shown that HDL is capable of removing cholesterol from cells Picardo et al., *Arteriosclerosis,* 6 (1986), 434–441). Data of this nature suggest that one antiatherogenic property of HDL may lie in its ability to deplete tissue of excess free cholesterol and eventually lead to the delivery of this cholesterol to the liver (Glomset, *J. Lipid Res.,* 9 (1968), 155–167). This has been supported by experiments showing efficient transfer of cholesterol from HDL to the liver (Glass et al., *Circulation,* 66 (*Suppl.* 1) (1982), 102; McKinnon et al.,*J. Biol, Chem.,* 261 (1986), 2548–2552). In addition, HDL may serve as a reservoir in the circulation for apoproteins necessary for the rapid metabolism of triglyceride-rich lipoproteins (Grow and Fried, *J. Biol Chem..* 2, (1978), 1834–1841; Lagocki and Scanu, *J. Biol. Chem.,* 255 (1980), 3701–3706; Schaefer et al., *J. Lipid Res.,* 23 (1982), 1259–1273). Accordingly, agents which increase HDL cholesterol concentrations would be of utility as anti-atherosclerotic agents, useful particularly in the treatment of dysliproteinimias and coronary heart disease.

PRIOR ART

U.S. Pat. No. 3,505,057 and U.S. Pat. No. 3,505,323 (E.I. DuPont de Nemours and Co, Apr. 7, 1970) disclose 1-aryl-tetrahydro-s-triazin-2[1H]-thiones and their use as herbicidal agents.

U.S. Pat. No 4,193,994 (Pfizer Inc., Mar. 18, 1980) discloses 1-(o-tolyl)-3,5-disubstituted tetrahydro-s-triazin-2 [1H]-thiones and their use as acaricidal agents.

*Zhurnal Obshchei Khimii,* Vol. 61, No. 8, (1991), pp. 1870–1873 , English translation (1992), pp. 1728–1730 (Plenum Publishing Co.), report the synthesis of 1-aryl-3, 5-di-(tert-butyl)-terahydro-triazin-2[1H]-thiones with no stated specific utility.

*Khim. Geterotsikl, Soedin.* (1986), pp. 976–980, reports the mass spectra of 1-aryl-3,5disubstituted-tetrahydro-triazin-2[1H]-thiones with no stated specific utility.

DESCRIPTION OF THE INVENTION

In accordance with this invention, there are provided 1-(aryl substituted)-3,5-disubstituted tetrahydro-triazin-2 [1H]-thiones which are useful as antiatherosclerotic agents.

More particularly, this invention provides antitherosclerotic agents of formula 1 having the structure

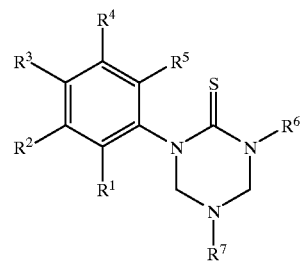

1 wherein $R^1$, $R^2$, $R^3$, $R^4$, and $R^5$ are each independently, hydrogen, halogen, alkyl of 1–6 carbon atoms, cycloalkyl of 3–8 carbon atoms, alkenyl of 2–7 carbon atoms, alkynyl of 2–7 carbon atoms, phenylalkyl of 7–10 carbon atoms, alkoxy of 1–6 carbon atoms, aryloxy of 7–12 carbon atoms, fluoroalkoxy of 1–6 carbon atoms, trifluoromethyl, alkylthio of 1–3 carbon atoms, alkylsulfonyl of 1–3 carbon atoms, —$SCF_3$, nitro, alkylamino in which the alkylamino moiety has 1–6 carbon atoms, or dialkylamino in which each alkyl group has 1–6 carbon atoms;

$R^6$ is hydrogen; and $R^7$ is alkyl of 1–6 carbon atoms, cycloalkyl of 3–8 carbon atoms, or arylalkyl of 7–12 carbon atoms or a pharmaceutically acceptable salt thereof.

With respect to the above compounds, it is preferred that $R^1$, $R^2$, $R^3$, $R^4$, and $R^5$ are each, independently, hydrogen, halogen, or alkyl of 1–6 carbon atoms.

This invention also provides a method of treating or inhibiting atherosclerosis, cardiovascular disease, or dyslipoproteinimias, and improving the HDL/LDL cholesterol ratio in a mammal in need thereof which comprises administering a compound of formula 1 having the structure

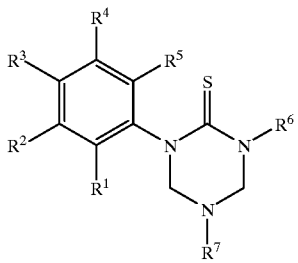

1 wherein

R[1], R[2], R[3], R[4], and R[5] are each independently, hydrogen, halogen, alkyl of 1–6 carbon atoms, cycloalkyl of 3–8 carbon atoms, alkenyl of 2–7 carbon atoms, alkynyl of 2–7 carbon atoms, phenylalkyl of 7–10 carbon atoms, alkoxy of 1–6 carbon atoms, aryloxy of 7–12 carbon atoms, fluoroalkoxy of 1–6 carbon atoms, trifluoromethyl, alkylthio of 1–3 carbon atoms, alkylsulfonyl of 1–3 carbon atoms, —SCF$_3$, nitro, alkylamino in which the alkylamino moiety has 1–6 carbon atoms, or dialkylamino in which each alkyl group has 1–6 carbon atoms;

R[6] is hydrogen, alkyl of 1–6 carbon atoms, cycloalkyl of 3–8 carbon atoms, or arylalkyl of 7–12 carbon atoms; and R[7] is alkyl of 1–6 carbon atoms, cycloalkyl of 3–8 carbon atoms, or arylalkyl of 7–12 carbon atoms or a pharmaceutically acceptable salt thereof.

With respect to the above methods, it is preferred that R[6] is alkyl of 1–6 carbon atoms; that R[6] is alkyl of 1–6 carbon atoms, and R[1], R[2], R[3], R[4], and R[5] are each, independently, hydrogen, halogen, or alkyl of 1–6 carbon atoms. It is more preferred that R[6] is methyl.

As used in describing this invention, the terms alkyl, alkenyl, and alkynyl include both straight chain as well as branched moieties. This includes the alkyl portions of substituents such as alkoxy, thioalkyl, alkylsulfinyl, alkylsulfonyl, fluoroalkoxy, and the like. The term halo includes fluorine, chlorine, bromine, and iodine. Fluoroalkoxy includes mono-, di-, tri-, and polyfluorinated alkoxy moieties such as —OCF$_3$, —OCH$_2$F, —OCHF$_2$, —OCH$_2$CF$_3$, and the like. The aryl moiety of the arylalkyl and aryloxy substituents include radicals such as benzyl, phenyl and naphthyl.

As used in describing this invention, the term "compounds of this invention" includes the broader description encompassing the formula used in accordance with the above methods, as well as the narrower description encompassing the formula used in accordance with the above novel compounds.

The pharmaceutically acceptable salts are those derived from organic and inorganic acids such as, but not limited to: acetic, lactic, citric, tartaric, succinic, fumaric, maleic, malonic, mandelic, malic, hydrochloric, hydrobromic, phosphoric, nitric, sulfuric, methanesulfonic, toluenesulfonic and similarly known acceptable acids.

The 1-(aryl substituted)-3,5-disubstituted tetrahydrotriazin-2[1H]thiones of this invention are preferentially prepared by reacting an appropriately substituted aromatic thiourea with formaldehyde and an amine (Mannich reaction; see J. Marsh, *Advanced Organic Chemistry*, 3rd Ed,, Wiley-Interscience, NY, page 800) as shown in Scheme 1.

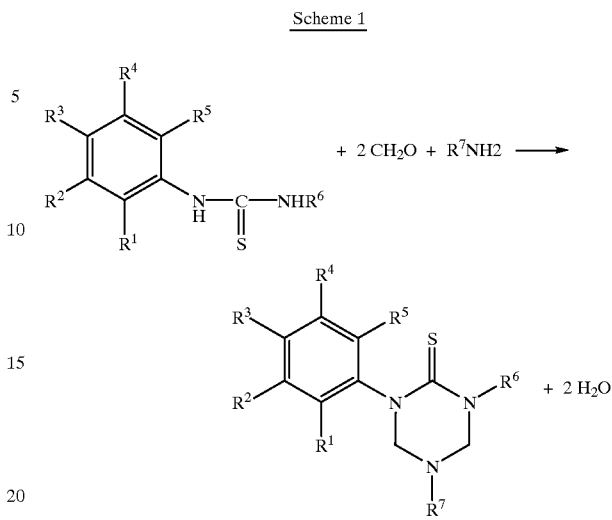

Scheme 1 wherein R[1], R[2], R[3], R[4], R5, R[6], and R[7] are as described above for formula 1.

The appropriately substituted aromatic thioureas starting materials are either available commercially or are known in the art or can be prepared by procedures analogous to those in the literature for known compounds (see J. Marsh, Advanced Organic Chemistry, 3rd Ed., Wiley-Interscience, NY, page 1174).

Representative compounds of this invention were evaluated in an in vivo standard pharmacological test procedure which measured the ability of the compounds of this invention to elevate HDL cholesterol levels. The following briefly describes the procedure used and results obtained. Male Sprague-Dawley rats weighing 200–225 g were housed two per cage and fed Purina Rodent Chow Special Mix 5001-S supplemented with 0.25% cholic acid and 1.0% cholesterol and water ad libitum for 8 days. Each test substance was administered to a group of six rats fed the same diet with the test diet mixed in as 0.005–0.1% of the total diet. Body weight and food consumption were recorded prior to diet administration and at termination. Typical doses of the test substances were 5–100 mg/kg/day.

At termination, blood was collected from anesthetized rats and the serum was separated by centrifugation. Total serum cholesterol was assayed using the Sigma Diagnostics enzymatic kit for the determination of cholesterol, Procedure No. 352, modified for use with ninety-six well microtiter plates. After reconstitutiton with water the reagent contains 300 U/l cholesterol oxidase, 100 U/l cholesterol esterase, 1000 U/l horse radish peroxidase, 0.3 mmoles/l 4aminoantipyrine and 30.0 mmoles/l p-hydroxybenzene sulfonate in a pH 6.5 buffer. In the reaction cholesterol was oxidized to produce hydrogen peroxide which was used to form a quinoneimine dye. The concentration of dye formed was measured spectrophotometrically by absorbance at 490 nm after incubation at 25° C. for 30 minutes. The concentration of cholesterol was determined for each serum sample relative to a commercial standard from Sigma HDL cholesterol concentrations in serum were determined by separation of lipoprotein classes by fast protein liquid chromatography (FPLC) by a modification of the method of Kieft et al. [*J. Lipid Res.,* 32 (1991), 859–866]. Using this methodology, 25 ml of serum was injected onto Superose 12 and Superose 6 (Pharmacia), in series, with a column buffer of 0.05 M Tris (2-amino-2-hydroxymethyl-1, 3-propanediol) and 0.15 M sodium chloride at a flow rate of 0.5 mL/min. The eluted sample was mixed on line with Boehringer-Mannheim cholesterol reagent pumped at 0.2 mL/min. The combined eluents were mixed and incubated on line through a knitted coil (Applied Biosciences) maintained at a temperature of 45° C. The eluent was monitored by measuring absorbance at 490 nm and gave a continous absorbance signal proportional to the cholesterol concentration. The relative concentration for each lipoprotein class was calculated as the percent of total absorbance. HDL cholesterol concentration in serum, was calculated as the percent of total cholesterol as determined by FPLC multiplied by the total serum cholesterol concentration.

Test compounds were administered at a dose of 100 mg/kg or as indicated in parenthesis (Table I). The duration of treatment was eight days. The results obtained in this standard pharmaceutical test procedure are shown below in Table 1.

TABLE I

| Compound of Example | HDL Cholesterol Level Increase (%) at 100 mg/Kg or as indicated |
|---|---|
| Example 1 | 169 |
| Example 2 | 369 |
| Example 3 | 145 |
| Example 4 | 478 (75) |
| Example 5 | 445 |
| Example 6 | 78 (75) |
| Example 7 | 94 (50) |
| Example 8 | 165 (50) |
| Example 9 | 170 (50) |
| Example 10 | 98 (50) |
| Example 11 | 345 (50) |
| Example 12 | 35 (50) |
| Example 13 | 67 (50) |
| Example 14 | 149 (50) |
| Example 15 | 145 (50) |
| Example 16 | 117 (50) |
| Example 17 | 275 |
| Example 18 | 63 (50) |
| Example 19 | 116 (50) |
| Example 20 | 6 |
| Example 21 | 73 (50) |
| Example 22 | 27 (50) |
| Example 23 | 141 (50) |
| Example 24 | 187 (50) |
| Example 25 | 64 |
| Example 26 | 21 |

The results obtained in this standard pharmacological test procedure showed that the compounds of this invention raised the concentration of HDL cholesterol, and are therefore useful for treating or inhibiting atherosclerosis, cardiovascular disease, or dyslipoproteinimias, and improving the HDL/LDL cholesterol ratio, and several metabolic conditions associated with low concentrations of HDL such as low HDL-cholesterol levels in the absence of dyslipidemia, metabolic syndrome, non-insulin dependent diabetes mellitus (NIDMM), familial combined hyperlipidemia, familial hypertriglyceridemia, and dyslipidemia in peripheral vascular disease (PVD).

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets, preferably, contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is subdivided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analyusis and the patients recovery rate. By initiating the treatment regimen with a minimal daily dose of about one gram, the blood levels of HDL and the patient sympomatic relief analysis may be used to determine whether a larger dose is indicated. Based upon the data presented above, the projected daily dose for both human and veterinary use wil be from about 10 to about 200 milligrams/Kilogram per day. However, in general, satisfactory results are indicated to be obtained at daily dosages in the range of from 400 milligrams to about 2000 milligrams, conveniently administered in divided doses two to four times a day.

The following examples illustrate the preparation of representative compounds of this invention.

General Procedures for the preparation of Examples 1–26
Procedure A. To a mixture of the appropriately substituted thiourea (29.4 mmol) in EtOH (20 mL), is added 40% aqueous methylamine (32.3 mmol, 1.1 molar eq) and 37% aqueous formaldehyde (64.7 mmol, 2.2 molar eq). The solution is refluxed under nitrogen until complete by TLC (10% MeOH/CH$_2$Cl$_2$ or 2:1 Hex/EtOAc). The reaction mixture is cooled to room temperature and the precipitated product is filtered, washed with 50% aqueous ethanol and recrystallized, if necessary (recrystallization solvent provided in parenthesis);

Procedure B. Identical to procedure A except that the solvent is removed under vacuum and the residue is recrystallized (recrystallization solvent provided in parenthesis)

Procedure C. Identical to procedure A except that the reaction is run in water,

Procedure D. Identical to procedure A except that the solvent is removed under vacuum and the residue is chromatographed on silica gel eluting with 20% ethyl acetate in hexane;

Procedure E. Identical to procedure A except that the reaction is run in dioxane. The solvent is removed under vacuum and the residue is washed with water and recrystallized;

Procedure F. Identical to procedure A except that the reaction is run in dioxane. The solvent is removed under vacuum and residue is chromatographed on silica gel eluting with dichloromethane;

Procedure G. Identical to procedure A except that the reaction is run in dioxane. The reaction mixture is poured into water and extracted with dichloromethane. The extracts are evaporated in vacuo and the residue is chromatographed on silica gel with 30% ethyl acetate in hexane;

Procedure H: Identical to procedure G except that the desired product crystallizes directly upon concentration of the dichloromethane extracts.

EXAMPLE 1

1-(4Fluoro-phenyl-5-methyl-tetrahydro-1,3,5-triazin-2(1 H)-thione

Prepared in 74% yield according to procedure A described above; white solid, m.p. 173–175° C. (EtOH). Anal, Calcd. for $C_{10}H_{12}FN_3S$: C, 53.31; H, 5.37; N, 18.65. Found: C, 53.30; H, 5.36; N, 18.80.

EXAMPLE 2

5-Methyl-1-phenyl-tetrahydro-1,3,5triazin-2(1 H)-thione

Prepared in 65% yield according to procedure A described above; white solid, m.p. 175–176° C. (EtOH). Anal. Calcd for $C_{10}H_{13}N_3S$: C, 57.94; H, 6.32; N, 20.27. Found: C, 57.72; H, 6.27; N, 20.30.

EXAMPLE 3

1-(2,6-Dichloro-phenyl)-3-isobutyl-5-methyl-tetrahydro-1,3,5-triazin-2(1 H)-thione Prepared in 73% yield according to procedure B described above; white solid, m.p. 133–135° C. (heptane). Anal. Calcd. for $C_{14}H_{19}Cl_2N_3S$: C, 50.60; H, 5.76; N, 12.64. Found: C, 50.43; H, 5.68; N, 12.80.

EXAMPLE 4

1-(5-Chloro-2-methyl-phenyl)-5-methyl-tetrahydro-1,3,5-triazin-2(1 H)-thione

Prepared in 76% yield according to procedure A described above; white solid, m.p. 171–173° C. (EtOH). Anal. Calcd. for $C_{11}H_{14}ClN_3S$: C, 51.66; H, 5.52; N, 16.43. Found: C, 51.47; H, 5.51; N, 16.24.

EXAMPLE 5

1-(2,4-Dichloro-phenyl)-5-methyl-tetrahydro-1,3,5-triazin-2(1 H)-thione

Prepared in 66% yield according to procedure A described above; white solid m.p. 171–173° C. (EtOH). Anal. Calcd. for $C_{10}H_{11}ClN_3S$: C, 43.49; H, 4.01; N, 15.21. Found: C, 43.27; H, 3.87; N, 15.10.

EXAMPLE 6

1-(5-Chloro-2-methyl-phenyl)-3-isobutyl-5-methyl-tetrahydro-1,3,5,triazin-2(1 H)-thione Prepared in 57% yield according to procedure B described above; white solid, m.p. 110–112° C. (isopropyl ether). Anal. Calcd. for $C_{15}H_{22}ClN_3S$: C, 57.77; H, 7.11; N, 13.47. Found: C, 57.55; H, 7.13; N, 13.37.

EXAMPLE 7

1-(4-Methoxy-phenyl-5-methyl-tetrahydro-1,3,5-triazin-2(1 H)-thione

Prepared in 65% yield according to procedure A described above; white solid, m.p. 194° C. (MeOH). Anal. Calcd. for $C_{11}H_{15}N_3OS$: C, 55.67; H, 6.37; N, 17.71. Found: C, 56.04; H, 6.35; N, 17.84. Mass spectrum (PBEI, m/z): 237 $[M]^+$

EXAMPLE 8

1-(4-Chloro-phenyl)-5-methyl-tetrahydro-1,3,5-triazin-2(1 H)thione

Prepared in 83% yield according to procedure A described above; white solid, m.p. 178–179° C. (EtOH). Anal. Calcd. for $C_{10}H_{12}ClN_3S$: C, 49.68; H, 5.00; N, 17.38. Found: C, 49.75; H, 5.23; N, 17.20. Mass spectrum (PBEI, m/z): 241 $[M]^+$

EXAMPLE 9

1-(4-Nitro-phenyl)-5-methyl-tetrahydro-1,3,5-triazin-2(1 H)-thione

Prepared in 94% yield according to procedure A described above; yellow powder, m.p. 170–172° C. (EtOH). Anal. Calcd. for $C_{10}H_{12}N_4O_2S$: C, 47.61; H, 4.79; N, 22.21. Found: C, 47.43; H, 4.75: N, 22.25. Mass spectrum (EI, m/z): 252 $[M]^+$

EXAMPLE 10

1-(4-Dimethylamino-phenyl)-5-methyl-tetrahydro-1,3,5-triazin-2(1 H)-thione

Prepared in 52% yield according to procedure C described above; dark green solid, m.p. 173–175° C. (EtOH-H₂O). Anal. Calcd. for $C_{12}H_{18}N_4S$: C, 57.57; H, 7.25; N, 22.38. Found: C, 57.30; H, 7.15; N, 22.06. Mass spectrum (EI, m/z): 250 $[M]^+$

EXAMPLE 11

5-Methyl-1-(4-trifluoromethyl-phenyl)-tetrahydro-1,3,5-triazin-2(1 H)-thione

Prepared in 64% yield according to procedure A described above; white solid, m.p. 163–165° C. (EtOH). Anal. Calcd. for $C_{11}H_{12}F_3N_3S$: C, 48.03; H, 4.39; N, 15.26. Found: C, 48.03; H, 4.17; N, 15.47. Mass spectrum (EI, m/z): 275 $[M]^+$

EXAMPLE 12

5-Methyl-1-(4-methyl-phenyl-tetrahydro-1,3,5-triazin-2(1 H)-thione

Prepared in 86% yield according to procedure A described above; white solid, m.p. 176–178° C. (EtOH). Anal. Calcd.

for $C_{11}H_{15}N_3S$: C, 59.70; H, 6.83; N, 18.99. Found: C, 59.86; H, 6.92; N, 19.38. Mass spectrum (EI, m/z): 221 [MI]$^+$

EXAMPLE 13

1.5-Dimethyl-3-phenyl-tetrahydro-1,3,5-triazin-2(1 H)-thione

Prepared in 14% yield according to procedure B described above; white solid, m.p. 85–87° C. (isopropyl ether). Anal. Calcd. for $C_{11}H_{15}N_3S$: C, 59.70; H, 6.83; N, 18.89. Found: C, 59.92; H, 6.93; N, 18.75. Mass spectrum (PBEI, m/z): 221 [M]$^+$

EXAMPLE 14

1-(5-Chloro-2-methyl-phenyl)-3-ethyl-5-methyl-tetrahydro-1,3,5-triazin-2(1 H)-thione Prepared in 72% yield according to procedure A described above; white solid, m.p. 129–131° C. (EtOH). Anal. Calcd. for $C_{13}H_{18}ClN_3S$: C, 55.01; H, 6.39; N, 14.80. Found: C, 55.12; H, 6.40; N, 14.89. Mass spectrum (PBEI, m/z): 283/285 [M]$^+$

EXAMPLE 15

1-(5-Chloro-2-methyl-phenyl)-3,5-dimethyl-tetrahydro-1,3,5-triazin-2(1 H)-thione Prepared in 85% yield according to procedure A described above; white solid, m.p. 157–159° C. (EtOH). Anal. Calcd. for $C_2H_{16}ClN_3S$: C, 53.42; H, 5.98; N. 15.58. Found: C, 53.41; H, 5.89; N, 15.50. Mass spectrum (PBEI, m/z): $^{269}/_{271}$[M]$^+$

EXAMPLE 16

1-(5-Chloro-2-methyl-phenyl)-3-isopropyl-5-methyl-tetrahydro-1,3,5-triazin-2(1 H)-thione Prepared in 42% yield according to procedure D described above; white solid, m.p. 113–115° C. (petroleum ether-EtOAc). Anal. Calcd. for $C_{14}H_{20}ClN_3S$: C, 56.46; H, 6.77; N, 14.11. Found: C, 56.62; H, 6.76; N, 14.04. Mass spectrum (EI, m/z): $^{297}/_{299}$[M]$^+$

EXAMPLE 17

1-(4-Chloro-2-methyl-phenyl)3,5-dimethyl-tetrahydro-1,3,5-triazin-2(1 H)-thione

Prepared in 77% yield according to procedure E described above; white solid, m.p. 103–105° C. (isopropyl ether-EtOAc). Anal. Calcd. for $C_{12}H_{16}ClN_3S$: C, 53.42; H, 5.98; N, 15.58. Found; C, 53.41; H, 5.87; N, 15.48. Mass spectrum (EI, m/z): $^{269}/_{271}$[M$^+$

EXAMPLE 18

1-(4-Chloro-2-methyl-phenyl)-3-isopropyl-5-methyl-tetrahydro-1,3,5-triazin-2(1 H)-thione Prepared in 26% yield according to procedure D described above; white solid, m.p. 105–107° C. (petroleum ether-EtOAc). Anal. Calcd. for $C_{14}H_{20}ClN_3S$: C, 56.46; H, 6.77; N, 14.11. Found: C, 56.50; H, 6.84; N, 14.15. Mass spectrum (EI, m/z): $^{297}/_{299}$[M]$^+$

EXAMPLE 19

1-(4-Chloro-2-methyl-phenyl)-3-ethyl-5-methyl-tetrahydro-1,3,5-triazin-2(1 H)-thione Prepared in 31% yield according to procedure D described above; white solid, m.p. 90–92° C. ( petroleum ether-EtOAc). Anal. Calcd. for $C_{13}H_{18}ClN_3S$: C, 55.01; H, 6.39; N, 14.81. Found: C, 55.16; H, 6.35; N, 14.94. Mass spectrum (EI, m/z): $^{283}/_{285}$[M]$^+$

EXAMPLE 20

1-(4-Chloro-2-methyl-phenyl)-3-isobutyl-5-methyl-tetrahydro-1,3,5-triazin-2(1 H)-thione Prepared in 46% yield according to procedure D described above; white solid, m.p. 82–84° C. (petroleum ether-EtOAc). Anal. Calcd. for $C_{15}H_{22}ClN_3S$: C, 57.77; H, 7.1 1; N, 13.47. Found: C, 57.92; H, 7.15; N, 13.48. Mass spectrum (EI, m/z): $^{311}/_{313}$[M]$^+$

EXAMPLE 21

1-(5-Chloro-2-methyl-phenyl)-5-ethyl-3-methyl-tetrahydro-1,3,5-triazin-2(1 H)-thione Prepared in 64% yield according to procedure B described above; white solid, m.p. 93–95° C. (isopropyl ether-EtOAc). Anal. Calcd. for $C_{13}H_{18}ClN_3S$: C, 55.01; H, 6.39; N, 14.81. Found: C, 54.72; H, 6.33; N, 14.69. Mass spectrum (El, m/z): $^{283}/_{285}$[M]$^+$

EXAMPLE 22

1-(5-Chloro-2-methyl-phenyl)-5-isopropyl-3-methyl-tetrahydro-1,3,5-triazin-2(1 H)-thione Prepared in 59% yield according to procedure B described above; white solid, m.p. 83–85° C. (isopropyl ether). Anal. Calcd. for $C_{14}H_{20}ClN_3S$: C, 56.46; H, 6.77; N, 14.11. Found: C, 56.27; H, 6.69; N, 14.07. Mass spectrum (PBE, m/z): $^{297}/_{299}$[M]$^+$

EXAMPLE 23

1-(2,6-Dimethyl-phenyl)-3,5dimethyl-tetrahydro-1,3, 5-triazin-2(1 H)-thione

Prepared in 64% yield according to procedure B described above; white solid, m.p. 121–123° C. (isopropyl ether). Anal. Calcd. for $C_{13}H_{19}N_3S$: C, 62,61; H, 7.68; N, 16.85. Found: C, 62.30; H, 7.76; N, 16.90.

EXAMPLE 24

5-tert-Butyl-1-(5-chloro-2-methyl-phenyl)-3-methyl-tetrahydro-1,3,5,-triazin-2(1H)-thione Prepared in 53% yield according to procedure F described above; white solid, m.p. 130–132° C. (dichloromethane). Anal. Calcd. for $C_{15}H_{22}ClN_3S$: C, 57.77; H, 7.11; N, 13.47. Found: C, 57.84; H, 7.23; N, 13.54. Mass spectrum (EI, m/z): $^{311}/_{313}$[M]$^+$

EXAMPLE 25

5-Benzyl-1-(5-chloro-2-methyl-phenyl)-3-methyl-tetrahydro-1,3,5-triazin-2(1 H)-thione Prepared in 52% yield according to procedure G described above; white solid, m.p. 148–149° C. (hexane-EtOAc). Anal. Calcd. for $C_9H_{22}ClN_2S$: C, 62.50; H, 5.83; N, 121.15. Found: C, 62.27; H, 5.80; N, 11.98. Mass spectrum (EI, m/z): 345 [M]$^+$

EXAMPLE 26

1,5-Dibenzyl-3-(5-chloro-2-methyl-phenyl)-tetrahydro-1,3,5-triazin-2(1 H)-thione Prepared according to procedure H described above; white solid, m.p. 202–203° C. (dichloromethane). Anal.

Calcd. for $C_{18}H_{20}ClN_3S$: C, 68.31; H, 5.73; N, 9.96. Found: C, 68.10; H, 5.60; N, 9.68. Mass spectrum: (EI, m/z): 421 $[M]^+$

What is claimed is:

1. A method of treating or inhibiting atherosclerosis, cardiovascular disease, or dyslipoproteinimias in a mammal in need thereof which comprises administering to said mammal an effective amount of a compound of formula 1 having the structure

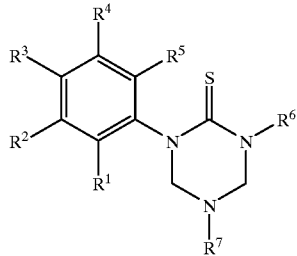

1 wherein $R^1$, $R^2$, $R^3$, $R^4$, and $R^5$ are each independently, hydrogen, halogen, alkyl of 1–6 carbon atoms, cycloalkyl of 3–8 carbon atoms, alkenyl of 2–7 carbon atoms, alkynyl of 2–7 carbon atoms, phenylalkyl of 7–10 carbon atoms, alkoxy of 1–6 carbon atoms, aryloxy of 7–12 carbon atoms, fluoroalkoxy of 1–6 carbon atoms, trifluoromethyl, alkylthio of 1–3 carbon atoms, alkylsulfonyl of 1–3 carbon atoms, $-SCF_3$, nitro, alkylamino in which the alkylamino moiety has 1–6 carbon atoms, or dialkylamino in which each alkyl group has 1–6 carbon atoms;

$R^6$ is hydrogen, alkyl of 1–6 carbon atoms, cycloalkyl of 3–8 carbon atoms, or arylalkyl of 7–12 carbon atoms; and $R^7$ is alkyl of 1–6 carbon atoms, cycloalkyl of 3–8 carbon atoms, or arylalkyl of 7–12 carbon atoms or a pharmaceutically acceptable salt thereof.

2. The method according to claim 1, wherein $R^6$ is alkyl of 1–6 carbon atoms.

3. The method according to claim 2, wherein $R^1$, $R^2$, $R^3$, $R^4$, and $R^5$ are each, independently, hydrogen, halogen, or alkyl of 1–6 carbon atoms.

4. The method according to claim 3, wherein $R^6$ is methyl.

5. The method according to claim 1 in which the compound administered is selected from the group consisting of 1-(4-chloro-2-methyl-phenyl)-3-isopropyl-5-methyl-tetrahydro-1,3,5-triazin-2(1 h)-thione, 1-(4-chloro-2-methyl-phenyl)-3-ethyl-5-methyl-tetrahydro-1,3,5-triazin-2(1 h)thione, 1-(4-chloro-2-methyl-phenyl)-3-isobutyl-5-methyl-tetrahydro-1,3,5-triazin-2(1 h)-thione, 1-(5-chloro-2-methyl-phenyl)-5-ethyl-3-methyl-tetrahydro-1,3,5-triazin-2(1 h)-thione,1-(5-chloro-2-methyl-phenyl)-5-ethyl-3-methyl-tetrahydro-1,3,5-triazin-2(1 h)-thione, 1-(5-chloro-2-methyl-phenyl)-5-isopropyl-3-methyl-tetrahydro-1,3,5-triazin-2(1 h)-thione, 1-(2,6-dimethyl-phenyl)-3,5-dimethyl-tetrahydro-1, 3,5-triazin-2(1 h)-thione, 5-tert-butyl-1-(5-chloro-2-methyl-phenyl)-3-methyl-tetrahydro-1,3,5-triazin-2(1 h)-thione, 5-benzyl-1-(5-chloro-2-methyl-phenyl)-3-methyl-tetrahydro-1, 3,5-triazin-2(1 h)-thione, and 1,5-dibenzyl-3-(5-chloro-2-methyl-phenyl)-tetrahydro-1, 3,5-triazin-2(1 h)-thione, or a pharmaceutically acceptable salt of thereof.

6. A method of increasing HDL cholesterol levels in a mammal in need thereof, which comprises administering to said mammal an effective amount of a compound of formula 1 having the structure

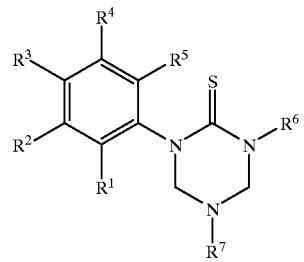

1 wherein $R^1$, $R^2$, $R^3$, $R^4$, and $R^5$ are each independently, hydrogen, halogen, alkyl of 1–6 carbon atoms, cycloalkyl of 3–8 carbon atoms, alkenyl of 2–7 carbon atoms, alkynyl of 2–7 carbon atoms, phenylalkyl of 7–10 carbon atoms, alkoxy of 1–6 carbon atoms, aryloxy of 7–12 carbon atoms, fluoroalkoxy of 1–6 carbon atoms, trifluoromethyl, alkylthio of 1–3 carbon atoms, alkylsulfonyl of 1–3 carbon atoms, $-SCF_3$, nitro, alkylamino in which the alkylamino moiety has 1–6 carbon atoms, or dialkylamino in which each alkyl group has 1–6 carbon atoms;

$R^6$ is hydrogen, alkyl of 1–6 carbon atoms, cycloalkyl of 3–8 carbon atoms, or arylalkyl of 7–12 carbon atoms; and $R^7$ is alkyl of 1–6 carbon atoms, cycloalkyl of 3–8 carbon atoms, or arylalkyl of 7–12 carbon atoms or a pharmaceutically acceptable salt thereof.

7. A method of treating a condition associated with low levels of HDL cholesterol selected from the group consiting of metabolic syndrome, non-insulin dependent diabetes mellitus, familial combined hyperlipidemia, or familial hypertriglyceridemia in a mammal in need thereof, which comprises administering to said mammal an effective amount of a compound of formula 1 having the structure

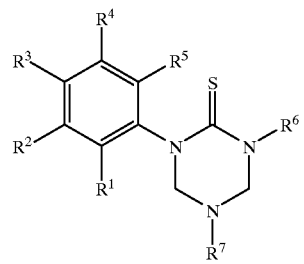

1 wherein $R^1$, $R^2$, $R^3$, $R^4$, and $R^5$ are each independently, hydrogen, halogen, alkyl of 1–6 carbon atoms, cycloalkyl of 3–8 carbon atoms, alkenyl of 2–7 carbon atoms, alkynyl of 2–7 carbon atoms, phenylalkyl of 7–10 carbon atoms, alkoxy of 1–6 carbon atoms, aryloxy of 7–12 carbon atoms, fluoroalkoxy of 1–6 carbon atoms, trifluoromethyl, alkylthio of 1–3 carbon atoms, alkylsulfonyl of 1–3 carbon atoms, $-SCF_3$, nitro, alkylamino in which the alkylamino moiety has 1–6 carbon atoms, or dialkylamino in which each alkyl group has 1–6 carbon atoms;

$R^6$ is hydrogen, alkyl of 1–6 carbon atoms, cycloalkyl of 3–8 carbon atoms, or arylalkyl of 7–12 carbon atoms; and $R^7$ is alkyl of 1–6 carbon atoms, cycloalkyl of 3–8 carbon atoms, or arylalkyl of 7–12 carbon atoms
or a pharmaceutically acceptable salt thereof.

8. A pharmaceutical composition which comprises a compound of formula 1 having the structure

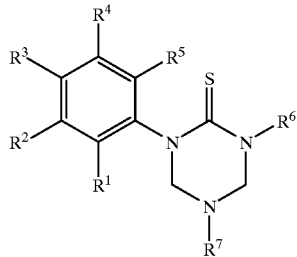

wherein $R^1$, $R^2$, $R^3$, $R^4$, and $R^5$ are each independently, hydrogen, halogen, alkyl of 1–6 carbon atoms, cycloalkyl of 3–8 carbon atoms, alkenyl of 2–7 carbon atoms, alkynyl of 2–7 carbon atoms, phenylalkyl of 7–10 carbon atoms, alkoxy of 1–6 carbon atoms, aryloxy of 7–12 carbon atoms, fluoroalkoxy of 1–6 carbon atoms, trifluoromethyl, alkylthio of 1–3 carbon atoms, alkylsulfonyl of 1–3 carbon atoms, —$SCF_3$, nitro, alkylamino in which the alkylamino moiety has 1–6 carbon atoms, or dialkylamino in which each alkyl group has 1–6 carbon atoms;

$R^6$ is hydrogen; and $R^7$ is alkyl of 1–6 carbon atoms, cycloalkyl of 3–8 carbon atoms, or arylalkyl of 7–12 carbon atoms or a pharmaceutically acceptable salt thereof and a pharmaceutical carrier.

* * * * *